United States Patent
Sawyer et al.

(10) Patent No.: US 11,298,436 B2
(45) Date of Patent: Apr. 12, 2022

(54) METHODS AND SYSTEMS FOR STERILIZING SURGICAL DRAINS

(71) Applicant: Duke University, Durham, NC (US)

(72) Inventors: Charlotte Lynne Sawyer, Durham, NC (US); Yitaek Azariah Hwang, Durham, NC (US); Michaela Jane Walker, Durham, NC (US); Vaibhav Bajaj, Durham, NC (US); Scott Thomas Hollenbeck, Durham, NC (US)

(73) Assignee: Duke University, Durham, NC (US)

(*) Notice: Subject to any disclaimer, the term of this patent is extended or adjusted under 35 U.S.C. 154(b) by 256 days.

(21) Appl. No.: 16/475,855

(22) PCT Filed: Jan. 3, 2018

(86) PCT No.: PCT/US2018/012206
§ 371 (c)(1),
(2) Date: Jul. 3, 2019

(87) PCT Pub. No.: WO2018/129060
PCT Pub. Date: Jul. 12, 2018

(65) Prior Publication Data
US 2019/0343973 A1 Nov. 14, 2019

Related U.S. Application Data

(60) Provisional application No. 62/441,666, filed on Jan. 3, 2017.

(51) Int. Cl.
*A61L 2/10* (2006.01)
*A61L 2/24* (2006.01)
*A61M 1/00* (2006.01)

(52) U.S. Cl.
CPC ............ *A61L 2/10* (2013.01); *A61L 2/24* (2013.01); *A61M 1/67* (2021.05); *A61L 2202/11* (2013.01); *A61L 2202/121* (2013.01); *A61L 2202/122* (2013.01); *A61L 2202/14* (2013.01); *A61L 2202/24* (2013.01); *A61M 2209/10* (2013.01)

(58) Field of Classification Search
CPC ........... A61L 2/10; A61L 2/24; A61L 2202/24
See application file for complete search history.

(56) References Cited

U.S. PATENT DOCUMENTS 8,747,764 B1 6/2014 Burchman et al.
2013/0226114 A1 8/2013 Mass et al.
(Continued)

FOREIGN PATENT DOCUMENTS

CN 204193141 3/2015

*Primary Examiner* — Kevin Joyner
(74) *Attorney, Agent, or Firm* — Polsinelli PC (57) ABSTRACT

Systems and methods for decontaminating a surgical drain and its reservoir are provided. An apparatus is provided in the form of a container having an interior chamber and an expansible opening to the interior chamber for insertion of a surgical drain therethrough. Ultraviolet light emitters are disposed within the interior chamber to emit beams of ultraviolet radiation at the surgical drain and/or its reservoir, thereby killing or neutralizing bacteria and fungus on the drain. Walls forming the expansible opening are collapsible to abut a portion of the inserted drain when inserted into the apparatus, and a fluid tight seal is formed between the drain and the apparatus.

10 Claims, 5 Drawing Sheets

(56) References Cited

U.S. PATENT DOCUMENTS

2015/0209457 A1* 7/2015 Bonutti .................... A61L 2/10
                                                            250/435
2016/0324996 A1* 11/2016 Bilenko .................... A61L 2/24

* cited by examiner

METHODS AND SYSTEMS FOR STERILIZING SURGICAL DRAINS

CROSS-REFERENCE TO RELATED APPLICATIONS

This application is a U.S. national phase under 35 U.S.C. § 371 of International Patent Application No. PCT/US2018/012206 filed on Jan. 3, 2018, which claims priority of U.S. Provisional Patent Application Ser. No. 62/441,666 filed on Jan. 3, 2017, which are hereby incorporated by reference in their entirety.

BACKGROUND

Treatment of various health conditions, such as diseases or injuries, can involve surgery. Surgery typically requires healing time, and post operative recovery procedures aim to provide for fast and uneventful healing.

However, issues can arise during the post operative recovery phase. Fluids that collect in a wound can lead to a seroma. A seroma can create an environment for bacteria growth, wherein a surgical site infection (SSI) could develop. SSI is the most common healthcare-associated infection, and can result in increased hospital readmission rates, longer hospital stays, increased admissions to the intensive care unit (ICU), increased antibiotic use, delayed wound healing, long term complications at the site, and even death.

One tool to attempt to reduce the risk of development of a seroma is the surgical drain. A surgical drain actively drains fluid which collects in a wound bed after surgery, preventing seroma formation which can aid in the healing process. The surgical drain relieves fluid from the surrounding wound bed and prevents bacteria growth from forming inside the body, thereby decreasing the risk of infection. Depending on the amount of drainage, a patient may have a surgical drain in place for one day or up to several weeks.

However, surgical drains have a number of associated problems. Surgical drains must be emptied daily by nurses or patients themselves and are known to become contaminated with bacteria and fungus. The longer a drain stays in a patient the higher there is a risk for infection as they provide a pathway for bacteria to enter the body. Closed drain systems, which do not require emptying, have more precautions against infection than open drains, but there remains room for improvement.

Currently, there is no established method for cleaning or sterilizing drains.

SUMMARY

In accordance with the present invention, systems and methods are defined for decontaminating a surgical drain (herein defined as drain tubing and/or a collecting reservoir) using a device that emits ultraviolet light. In one example embodiment, an apparatus for decontaminating a surgical drain is provided. The apparatus comprises a body having one or more sidewalls and a bottom that define an interior, an expansible opening to the interior for insertion of a surgical drain therethrough, and one or more ultraviolet light emitters disposed within the interior. An interior surface of the apparatus collapses to abut a portion of the inserted drain, forming a tight seal between the interior surface of the apparatus and the portion of the inserted drain.

In another example embodiment, a medical drainage system is provided. The system comprises a surgical drain device comprising a compression bulb and a tube, wherein a first end of the tube is insertable into the bulb and a second end of the tube is insertable into a patient incision. The system further comprises a body having one or more sidewalls and a bottom that define an interior, an expansible opening to the interior for insertion of the surgical drain device therethrough, and one or more ultraviolet light emitters disposed within the interior. An interior surface of the apparatus collapses to abut a portion of the inserted surgical drain device, forming a tight seal between the interior surface of the apparatus and the portion of the inserted surgical drain device.

In another example embodiment, a method for decontaminating a surgical drain is provided. The method includes inserting a surgical drain into a container, wherein a portion of the surgical drain extends through an opening of the container. The method then includes closing the container opening, sealing the container around the portion of the surgical drain that extends through the opening, and applying ultraviolet radiation to the surgical drain within the container.

These as well as other aspects and advantages of the synergy achieved by combining the various aspects of this technology, that while not previously disclosed, will become apparent to those of ordinary skill in the art by reading the following detailed description, with reference where appropriate to the accompanying drawings.

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein. Unless otherwise defined, the technical terms used herein have the same meaning as commonly understood by one of ordinary skill in the art.

As used herein, the terms "subject" and "patient" are interchangeable and refer to both human and nonhuman animals. In certain embodiments, the subject is a human patient having undergone a surgical procedure. In certain embodiments, the subject has a surgical drain evacuator bulb inserted into the subject's body at or near a surgical site.

As used herein, the term "bacteria" is illustrative of any type of biological contaminant that is able to be neutralized or killed through exposure to ultraviolet radiation.

I. OVERVIEW

A surgical drain device is used to remove fluids that build up in areas of a patient's body after surgery or when a patient has an infection. The surgical drain device typically comprises two parts: (i) tubing, which is coupled to (ii) a squeeze bulb having a generally round or grenade-like shape. In some embodiments, the surgical drain device may be a Jackson-Pratt drainage system (JP drain). The tubing may be made from rubber or other flexible material, and may have a flat or a round cross-section. When the squeeze bulb is compressed (squeezed) with a stopper in place to close off an outlet port in the bulb, a suction is generated.

The systems, apparatuses, and methods described herein meet a clinical need for decontamination of surgical drain devices by way of application of ultraviolet light emitters, where ultraviolet radiation application to a surgical drain device is used to neutralize bacterial and fungal contamination on the device. While a portion of the tubing of a surgical drain remains inside the subject, the surgical bulb and exterior part of the tubing are placed within a decontamination apparatus and are exposed to one or more ultraviolet light sources, with the resulting radiation causing decontamination of bacteria or microorganisms. The present disclosure advantageously provides for the ability to clean an existing, on the market surgical drain device. Further, the present disclosure advantageously provides for decontamination of a surgical drain device while the device remains inserted in a patient, thereby minimizing or eliminating any disruption in use of the device. The decontamination system disclosed herein could be applied to decontaminate various other medical devices as well.

In some example embodiments, decontamination means disinfection of the surgical drain bulb and/or associated tubing, wherein harmful microorganisms are reduced or eliminated.

In some example embodiments, decontamination means sterilization of the surgical bulb and/or associated tubing, wherein all microorganisms and their spores are destroyed or eliminated.

The systems, apparatuses, and methods described herein provide for improvement of surgical drain infection rate without having to redesign the surgical drain device.

Figure 1:
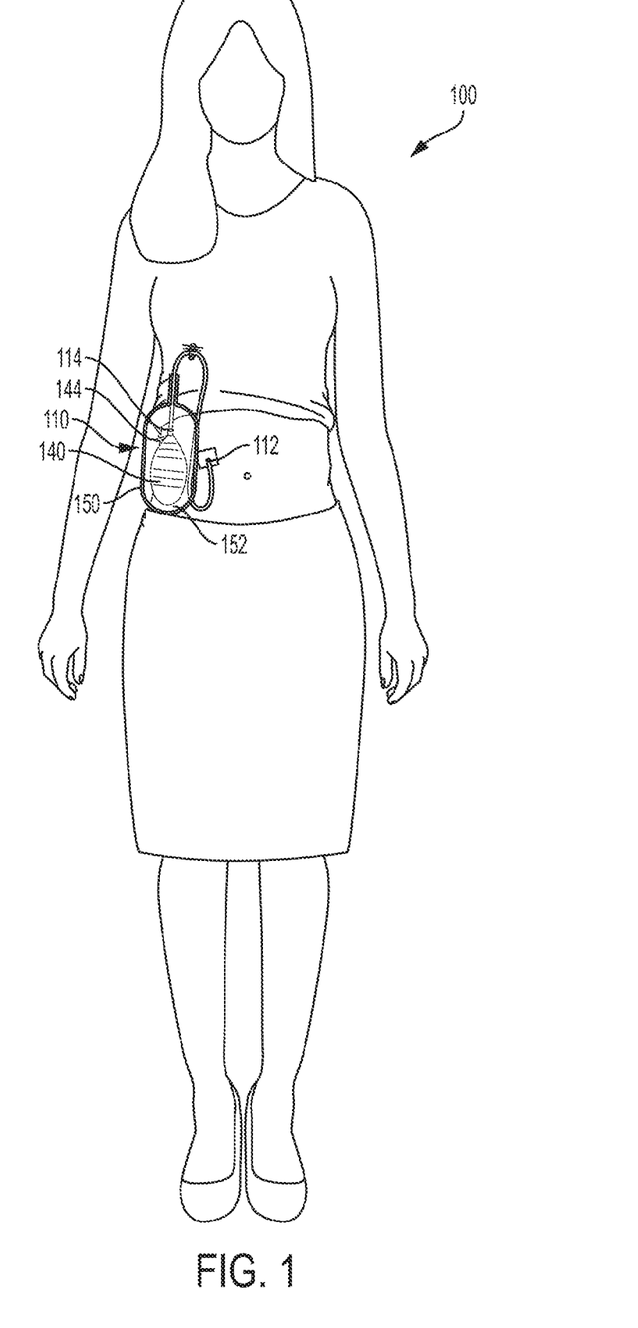
FIG. 1 depicts a drainage system for decontamination of a surgical drain while in use with a patient, in accordance with at least one example embodiment.

FIG. 1 depicts a drainage system 100 for decontamination of a surgical drain 110 while in use with a patient, in accordance with at least one example embodiment. A first end 112, known as a drainage end, of tubing 112 from the surgical drain 110 is placed within the patient. The tubing then exits through an incision in the patient and the second end 114 of the tubing is attached to a bulb 140. The bulb 140 includes an outlet port having a stopper 144 to close access to the outlet port.

A decontamination device 150 is also depicted. The decontamination device 150 is shown as having a chamber 152, within which the bulb 140 and at least a portion of the tubing 112 are maintained during a decontamination procedure. One or more ultraviolet light emitters are present in the chamber, emitting ultraviolet light to neutralize or kill bacteria on the bulb 140 and tubing 112. Further details and various embodiments for such a decontamination device are described with reference to FIGS. 2a-5 below.

II. EXAMPLE EMBODIMENTS

Figure 2A:
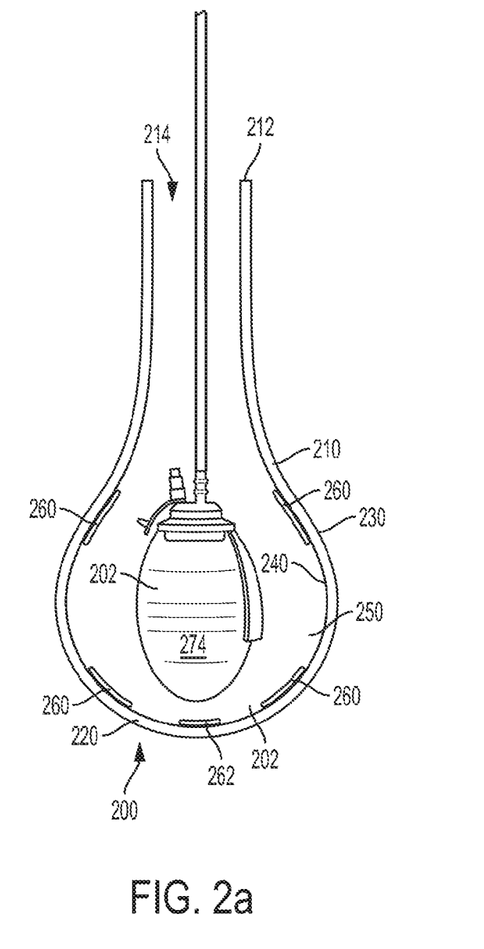
FIG. 2a depicts an apparatus in an open position for decontamination of a surgical drain, in accordance with at least one example embodiment.
Figure 2B:
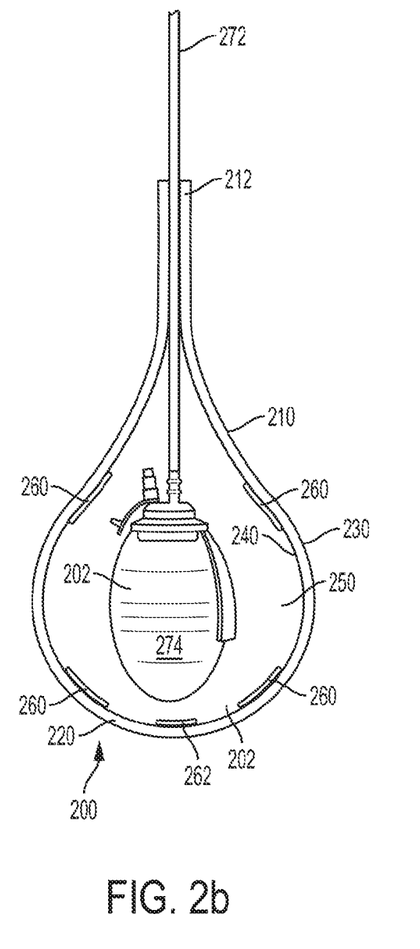
FIG. 2b depicts the apparatus of FIG. 2a in a closed position, in accordance with at least one example embodiment.

FIG. 2a depicts an apparatus 200 in an open position for decontamination of a surgical drain 202, in accordance with at least one example embodiment. In the embodiment shown in FIG. 2a, the apparatus 200 comprises a teardrop shaped container having a sidewall portion 210 and a bottom portion 220, both having an exterior surface 230, and an interior surface 240 that defines an interior chamber 250. The sidewall portion 210 and the bottom portion 220 are shown to be formed integrally in the embodiment of FIGS. 2a-b. The bottom portion 220 is shown in the embodiment of FIGS. 2a-b as having an arced or semi-circular shape. The sidewall portion 210 is shown in the open position to have an end 212 forming a perimeter of an expansible opening 214 opposite the bottom 220. The expansible opening 214 may serve as a pass-through for medical devices, such as surgical drains for example.

In some example embodiments, the apparatus 200 is made of a flexible material. The apparatus 200 may be a malleable container. In other example embodiments, the apparatus 200 is made of a rigid material. The material forming the apparatus 200 is preferably a UV impermeable material.

Ultraviolet emitting light sources 260 are depicted in FIG. 2a, affixed to the interior surface 240 of the sidewall portion 210 and bottom portion 220. In one example embodiment, the light sources 260 take the form of strips connected to a power source, such as one or more batteries 262. The strips may be flexible strips so as to conform to the interior surface of the apparatus 200 and, in embodiments wherein the apparatus 200 is made of a flexible material and can bend, the flexible strips can bend along with the apparatus 200. In some example embodiments, only one ultraviolet light source is present.

Figure 5:
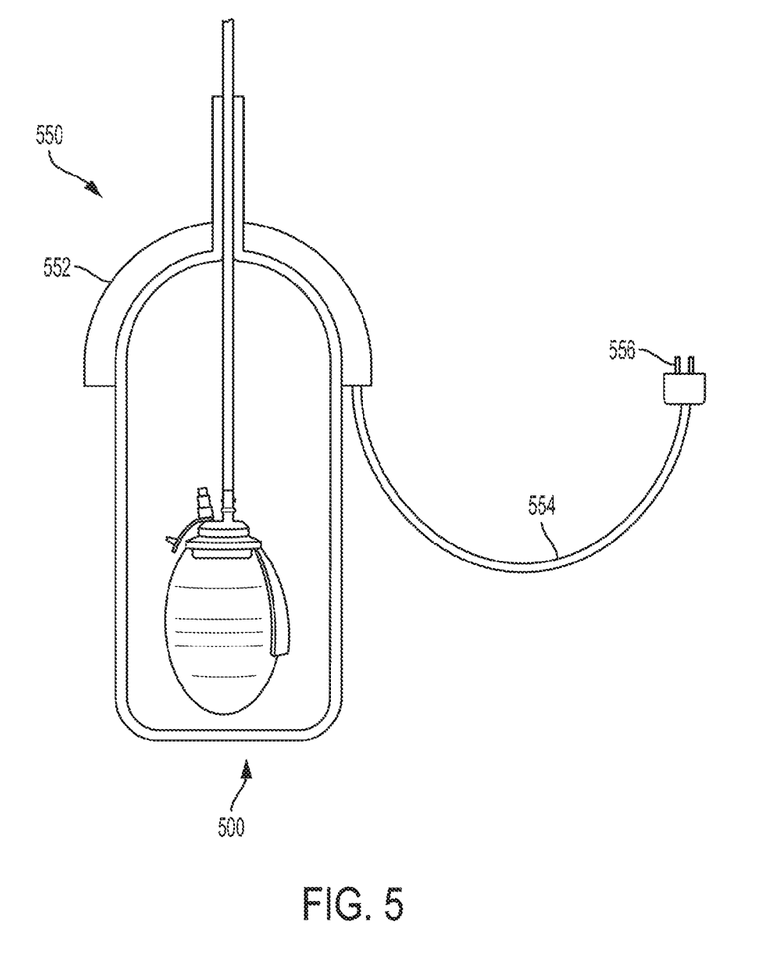
FIG. 5 depicts an apparatus for decontamination of a surgical drain, in accordance with at least one example embodiment.

The batteries 262 may be housed in a compartment on the apparatus 200. Other power sources or combinations of power sources may also be envisioned. In some embodiments, the power source may be a plug that plugs directly into an electrical outlet, or a rechargeable battery that plugs directly into an electrical outlet for charging, as depicted in FIG. 5 below.

FIG. 2b depicts the apparatus 200 of FIG. 2a in a closed position with a surgical drain device 270 contained therein, in accordance with at least one example embodiment. The closed position shown in FIG. 2b is the position ready for a decontamination procedure. It can be seen in the closed position of FIG. 2b that the interior surface 240 of the sidewall portion 210 at and near the end 212 abuts the tubing 272 for a sealing fit. It is preferable that no air escape from the opening 214 to the exterior environment while the apparatus 200 is in the closed position, and that a fluid tight seal is formed around the tubing 272. In the closed position, the apparatus 200 forms a teardrop shape, with sidewall portion 210 narrowing towards the end 212 until part of the sidewall portion 210 abuts the tubing 272, at which point the sidewall portion 210 extends substantially parallel to the tubing 272 to conform to the tubing walls and form a seal around the tubing 272.

A fastener may additionally be positioned on the apparatus 200 to ensure prevention of exposure of UV radiation to the outside. The fastener may include a zipper, a snap, clamps, and the like.

In operation, the opening 214 is expanded to reveal the interior of chamber 250, as shown in FIG. 2a. A bulb 274 of the surgical drain device 270 is lowered through the opening 214 and into the interior chamber 250. Once the bulb 274 and associated tubing 272 of the drain device 270 are in the desired position within the interior chamber 250, the sidewall portion 210 at or near the end 212 is moved toward the tubing 272 to form a seal around the tubing. Ultraviolet light emitters are then activated, with beams of ultraviolet light being directed at the bulb 274 and tubing 272 within the interior chamber 250. In some example embodiments, the ultraviolet light emitters comprise a UVC radiation source emitting UVC rays in the range of 100-280 nm. In some embodiments, a fastening or locking mechanism prevents the ultraviolet light emitters from being turned on unless there is a complete seal along the entire exterior diameter of the drainage tube at the point of the seal with the apparatus. The ultraviolet rays can pass through a silicone elastomer, of which surgical drains are generally made. The seal and any associated fastener are designed to not impede in the suction of fluids during decontamination. That is, the tubing is not squeezed or closed off during a decontamination procedure.

When application of ultraviolet radiation has been completed, the ultraviolet light emitters 260 are turned off and the sidewall portion 210 may then be removed from its sealing fit around the tubing.

In one example embodiment, a switch, button or other user-manipulable mechanism is used to turn on and off the ultraviolet light emitters 260. In other example embodiments, one or more sensors may be present on or in communication with the apparatus 200 to ensure operation only with a medical device properly installed within the interior chamber and a seal fit secured around the portion of the medical device (e.g., the tubing 272) extending through the opening 214. The one or more sensors may further communicate with the apparatus 200 to signal if a seal around the surgical device becomes compromised.

Alternative or additional mechanisms can be readily envisioned to ensure a sealing engagement between the sidewall portion 210 and the tubing 272.

An apparatus such as the apparatus 200 can be manufactured so as to be inexpensive enough for a patient to purchase the apparatus out of pocket if not covered by insurance. The seal prevents patients from exposure to significant ultraviolet radiation rendering the decontamination device and procedure safe for use in proximity to a patient.

Figure 3A:
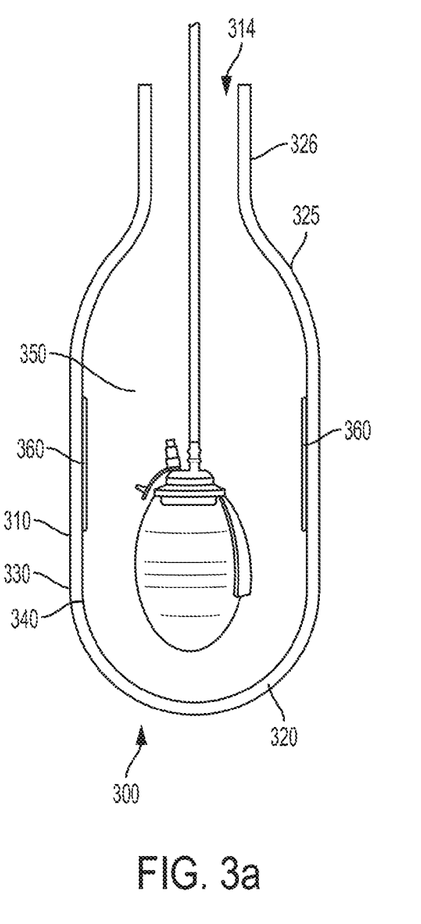
FIG. 3a depicts an apparatus in an open position for decontamination of a surgical drain, in accordance with at least one example embodiment.

FIG. 3a depicts an apparatus 300 in an open position for decontamination of a surgical drain, in accordance with at least one example embodiment. In the embodiment shown in FIG. 3a, the apparatus 300 comprises a container having a sidewall portion 310, a bottom portion 320, and a top portion 325, each having an exterior surface 330 and an interior surface 340 that defines an interior chamber 350. The sidewall portion 310, the bottom portion 320, and the top portion 325 are shown to be formed integrally. The bottom portion 320 is shown in the embodiment of FIG. 3a as having an arced or semi-circular shape. The sidewall portion 310 is shown in the embodiment of FIG. 3a as having a substantially straight cylindrical shape. The top portion 325 is shown in the embodiment of FIG. 3a as having an arced or semi-circular shape, with an expansible, fishmouth-style opening 314 formed by walls 326 extending from the apparatus 300. The opening 314 may serve as a pass-through for medical devices, such as surgical drains for example.

In some example embodiments, the apparatus 300 is made of a flexible material. The apparatus 300 may be a malleable container. In other example embodiments, the apparatus 300 is made of a rigid material.

Strips of ultraviolet emitting light sources 360 are depicted in FIG. 3a, affixed to the interior surface 340 of the sidewall portion 310. In other 20 embodiments, strips of ultraviolet emitting light sources may be present on any interior surface of the top portion 325, sidewall portion 310, or bottom portion 320. and the bottom portion 320. Similarly as described with the embodiments of FIGS. 2a-b, the ultraviolet light emitting strips are attached to a power source, such as one or more batteries or a power outlet.

Figure 3B:
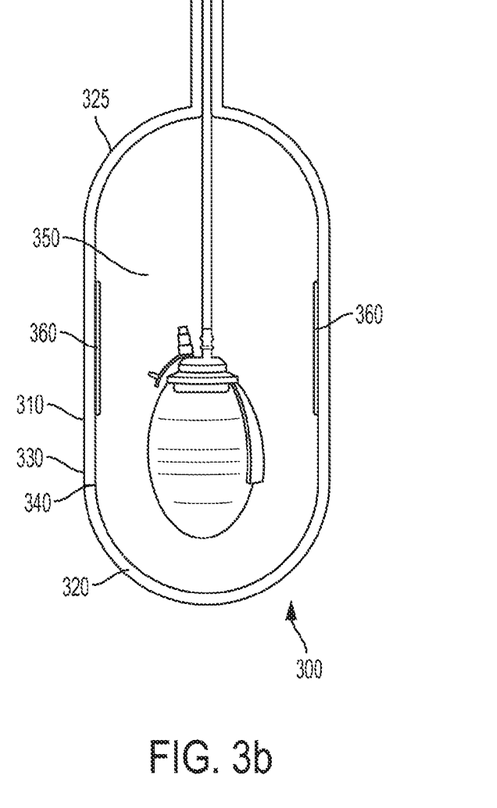
FIG. 3b depicts the apparatus of FIG. 3a in a closed position, in accordance with at least one example embodiment.

FIG. 3b depicts the apparatus 300 of FIG. 3a in a closed position for decontamination of a surgical drain, in accordance with at least one example embodiment.

Figure 4A:
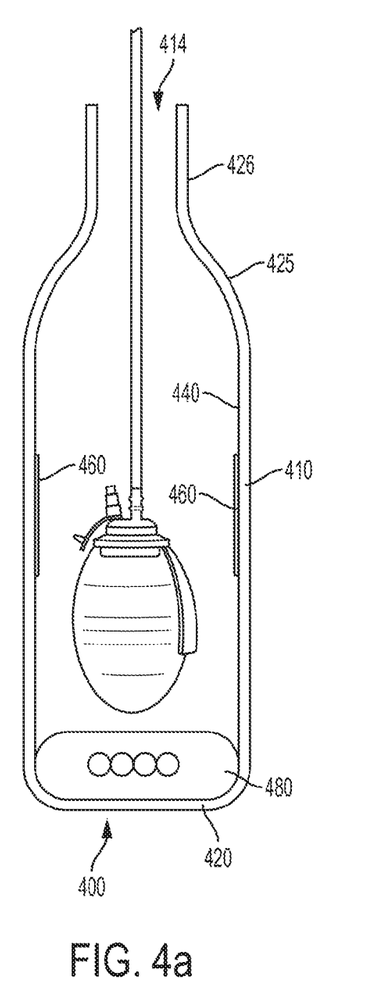
FIG. 4a depicts an apparatus in an open position for decontamination of a surgical drain, in accordance with at least one example embodiment.

FIG. 4a depicts an apparatus 400 in an open position for decontamination of a surgical drain, in accordance with at least one example embodiment. In the embodiment shown in FIG. 4a, the apparatus 400 comprises a container having a sidewall portion 410, a bottom portion 420, and a top portion 425, each having an exterior surface 430 and an interior surface 440 that defines an interior chamber 450. The sidewall portion 410, the bottom portion 420, and the top portion 425 are shown to be formed integrally. The bottom portion 420 is shown in the 35 embodiment of FIG. 4a as having a flat surface. The sidewall portion 410 is shown in the embodiment of FIG. 4a as having a substantially straight cylindrical shape, extending perpendicularly from the bottom portion 420. The top portion 425 is shown in the embodiment of FIG. 4a as having an arced or semi-circular shape, with an expansible, fishmouth-style opening 414 formed by walls 426 extending from the apparatus 400. The opening 414 may serve as a pass-through for medical devices, such as surgical drains for example.

In some example embodiments, the apparatus 400 is made of a flexible material. The apparatus 400 may be a malleable container. In other example embodiments, the apparatus 400 is made of a rigid material.

Strips of ultraviolet emitting light sources 460 are depicted in FIG. 4a, affixed to the interior surface 440 of the top portion 425, the sidewall portion 410 and the bottom portion 420. Similarly as described with the embodiments of FIGS. 2a-b, the ultraviolet light emitting strips are attached to a power source, such as one or more batteries or a power outlet.

Figure 4B:
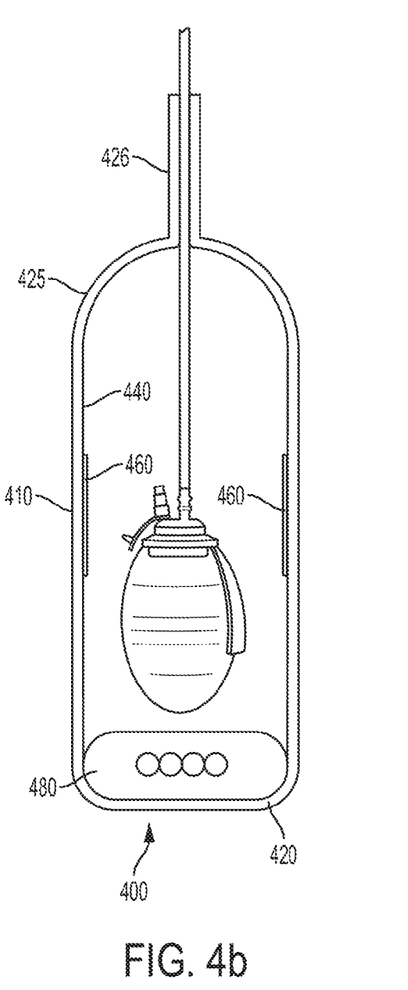
FIG. 4b depicts the apparatus of FIG. 4a in a closed position, in accordance with at least one example embodiment.

FIG. 4b depicts the apparatus 400 of FIG. 4a in a closed position for decontamination of a surgical drain, in accordance with at least one example embodiment.

A display panel 480 is shown on the apparatus 400 in FIG. 4a. The display panel 480 may include one or more of the following: one or more on buttons to initiate ultraviolet light emissions, one or more off buttons to stop ultraviolet light emissions, and an indicator. In some embodiments, the indicator may light up to indicate that the apparatus 400 is fluidly sealed and thus ready for ultraviolet light application. Various on and off buttons may be present to initiate or turn off different sections of ultraviolet light emitters. Although four buttons are shown in FIG. 4b, more or less buttons may be present on a display panel.

FIG. 4b depicts the apparatus 400 of FIG. 4a in a closed position for decontamination of a surgical drain, in accordance with at least one example embodiment.

FIG. 5 depicts an example power source 550 on an apparatus 500 for decontamination of a surgical drain, in accordance with at least one example embodiment. The power source 550 comprises an attachment portion 552 for affixing onto an exterior surface of the device 500, a cord 554 having a plug 556 at an end of the cord 554 to directly plug into an electrical outlet. Although the power source 550 is shown to be affixed to a top portion of the apparatus 500, the power source 550 may be affixed to the bottom portion or to the one or more sidewalls in various other embodiments.

Alternatively, a rechargeable battery having the capacity to plug directly into an electrical outlet to recharge may serve as the power source 550 depicted in FIG. 5.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. An apparatus for decontaminating a surgical drain comprising:
   a body having one or more sidewalls and a bottom that define an interior;
   an expansible opening to the interior for insertion of a surgical drain therethrough, the surgical drain comprising a compression bulb and a tube, wherein the interior is operable to receive the compression bulb at a portion of the tube when the surgical drain is inserted in a patient; and
   one or more ultraviolet light emitters disposed within the interior;
   wherein an interior surface of the apparatus collapses to abut a portion of the tube of the inserted surgical drain, forming a fluid tight seal between the interior surface of the apparatus and the tube of the inserted surgical drain,
   wherein the apparatus is operable to emit ultraviolet light from the one or more ultraviolet light emitters while the surgical drain remains inserted in the patient.

2. The apparatus of claim 1, wherein the one or more ultraviolet light emitters is affixed to the interior surface.

3. The apparatus of claim 1, further comprising a power source to provide power for activation of the one or more ultraviolet light emitters.

4. The apparatus of claim 1, wherein the ultraviolet light emitters emit UVC rays.

5. The apparatus of claim 1, wherein the one or more ultraviolet light emitters comprise flexible strips of material having ultraviolet light sources affixed thereto.

6. The apparatus of claim 1, wherein the interior is sized to receive the surgical drain therein with the surgical drain being spaced apart from the one or more sidewalls.

7. The apparatus of claim 1, wherein the body comprises a UV impenetrable material.

8. The apparatus of claims 1, further comprising a locking mechanism to secure the fluid tight seal.

9. The apparatus of claim 1, further comprising a sensor to determine whether the apparatus is sealed to the portion of the surgical drain prior to activation of the ultraviolet light emitters.

10. The apparatus of claim 9, wherein the ultraviolet light emitters are prevented from activating until receiving a signal from the sensor that a complete seal is formed around the portion of the surgical drain.

* * * * *